United States Patent [19]

Carr et al.

[11] Patent Number: 5,739,367
[45] Date of Patent: Apr. 14, 1998

[54] COBALT CATALYST

[75] Inventors: John Frederick Carr, Abbeymead; Derek Pakenham, Headingley Leeds, both of United Kingdom

[73] Assignee: Rhone-Poulenc Chemicals Ltd., Hertfordshire, United Kingdom

[21] Appl. No.: 817,295

[22] PCT Filed: Aug. 14, 1996

[86] PCT No.: PCT/GB96/01986

§ 371 Date: Jul. 21, 1997

§ 102(e) Date: Jul. 21, 1997

[87] PCT Pub. No.: WO97/07124

PCT Pub. Date: Feb. 27, 1997

[30] Foreign Application Priority Data

Aug. 15, 1995 [GB] United Kingdom ............ 9516683
Mar. 5, 1996 [GB] United Kingdom ............ 9604721

[51] Int. Cl.⁶ .................................................. C07F 15/06
[52] U.S. Cl. ........................ 556/147; 556/148; 556/149; 502/150
[58] Field of Search ........................ 556/147, 148, 556/149

[56] References Cited

U.S. PATENT DOCUMENTS 5,559,261  9/1996  Sivik ............................ 556/148
5,581,005  12/1996  Perkins ........................ 556/148

FOREIGN PATENT DOCUMENTS 2 034 061  5/1980  United Kingdom.

OTHER PUBLICATIONS

Kirschner et al., "The Effects of Ion Association on the Optical Rotary Dispersion of Coordination Compounds", Chemical Abstracts, 64(13):18452a (1966).
Jackman et al., "Synthesis of Transition–Metal Carboxylato Complexes[1,2]", Inorganic Chemistry, 18(6):1497–1502 (1979).
Wierenga et al., "Synthesis and Characteristics of Cobalt(III) Nicotinic Acid Complexes", Inorganic Chemistry, 21:2881–2885 (1992).

Primary Examiner—Porfirio Nazario-Gonzalez
Attorney, Agent, or Firm—Finnegan, Henderson, Farabow, Garrett & Dunner, L.L.P.

[57] ABSTRACT

A process for preparing a cobalt (III) complex is described which comprises: (i) treating a divalent cobalt salt of formula $Co^{II}X_{2/n}$ where n is the valency of an anion X, with up to 15 molar equivalents of ammonia or an amine; (ii) oxidizing the resulting amine complex; (iii) converting the oxidized complex to the corresponding carboxylate of formula $[Co^{III}(NR_3)_5R^1COO]X_{2/n}$ where each R, which may be the same or different, represents hydrogen or an optionally substituted hydrocarbon group and $R^1$ represents an alkyl or alkenyl group of 1 to 18 carbon atoms, at a pH above 8.5; and optionally (iv) replacing the X ion by a different anion by a metathetical reaction.

15 Claims, No Drawings

COBALT CATALYST

This application was filed under 35 U.S.C. 371 as a request for U.S. examination of International application No. PCT/GB96/01986, filed on Aug. 14, 1996.

This invention relates to a process for the preparation of cobalt complexes and to cobalt complexes obtained thereby.

Complexes of $Co^{III}$ act as oxidation catalysts and therefore promote reaction of various oxygen species. These reactions generally occur in water or an aqueous medium. Thus cobalt complexes are useful as oxidation catalysts or promoters of oxidation reactions with atmospheric oxygen or oxygen transfer agents such as peroxides, per iodates and amine oxides. A particular use of trivalent cobalt complexes is as bleaching catalysts for the activation of, for example, perborates.

The cobalt complexes originally proposed possessed an inner chloride anion but these have been found to be to prone to hydrolysis such that the complexes with an acetate inner anion are more useful. These acetato cobalt complexes are preferred for reactions in water since they give rise to less side reactions. This is because there is less hydrolysis or degradation of the catalyst and also less precipitation of such products which can give rise to fouling etc.

A typical acetato cobalt complex has the formula $[Co(NH_3)_3]Cl_2$ (hereafter referred to a PAAC). The starting material for the preparation of such a complex is cobalt chloride which has the formula $[Co^{II}(H_2O)_6]Cl_2$. Reaction with ammonia or an amine gives rise to the corresponding amino complex which, an oxidation, produces the compound of the formula $[Co^{III}(NH_3)_5H_2O]Cl_3$ (hereafter referred to as PAQC) together with $[Co^{III}(NH_3)_6]Cl_3$ (HAC). Reaction of PAQC with hot hydrochloric add gives rise to $[Co^{III}(NH_3)_5Cl]Cl_2$ (PACC). This PACC can be converted into the desired PAAC although very dilute solutions have to be used, which are clearly unrealistic on an industrial scale. Clearly it would be much better if a process could be found whereby cobalt chloride is converted into the desired acetato cobalt complex without the need to prepare PACC as an intermediate. Previous attempts at this have, though, been found to be unsatisfactory and have produced the desired compound in only very small yield. A way has now been found, according to the present invention, whereby such complexes can be prepared in good yield by controlling the amount of ammonia or amine. It has been found that control of the amount of ammonia or amine employed has a significant effect on the percent conversion to the desired PAAC.

According to the present invention, there is provided a process for preparing a cobalt II complex which comprises:
(i) treating a divalent cobalt salt of formula $Co^{II}X_{2/n}$ where n is the valency of an anion X, with up to 15 molar equivalents of ammonia or an amine;
(ii) oxidising the resulting amine complex;
(iii) converting the oxidised complex to the corresponding carboxylate of formula $[Co^{III}NR_3)_5R^1COO]X_{2/n}$ where each R, which may be the same or different, represents hydrogen or an optionally substituted hydrocarbon group and $R^1$ represents an alkyl or alkenyl group of 1 to 18, especially 1 to 6, carbon atoms, preferably methyl, at a pH above 8.5; and optionally
(iv) replacing the X ion by a different anion by a metathetical reaction.

As indicated above, a typical starting material is cobaltous chloride. This has the disadvantage that in the strongly oxidising conditions used to produce cobalt (III) oxide, the chloride counter ions may react to form potentially hazardous chlorine. Accordingly it is preferable to use cobaltous acetate as the starting material. Other starting materials include the oxide and hydroxide. It will be appreciated that the nature of the anion in the starting material is significant. Thus the use of cobaltous chloride will tend to give rise to the production of some PACC. The complex typically is an ammonium complex i.e. one in which R represents hydrogen. This is obtained by using ammonia but it will be appreciated that corresponding amino complexes can be obtained by reaction with amines having for example, 1 to 8, especially 1 to 6, carbon atoms, including alkyl amines such as methylamine and ethylamine, aromatic amines such as phenylamine, and cyclic amines such as cyclohexylamine as well as hydroxy amines such as ethanolamine as well as polyamines, typically diamines, such as ethylenediamine. Thus R can represent a hydrocarbon group which may itself be substituted by an amino group in which case the number of R groups present will be reduced below 5 in order to balance the molecule. For simplicity, the expression "amine" will be used herein to denote ammonia as well as aliphatic and aromatic amines.

In the step (i) of the process, typically an aqueous ammonia (or amine) solution is used to react with an aqueous solution of the cobalt salt. This reaction should be allowed to proceed slowly since it is significantly exothermic. Desirably an ammonium salt, typically ammonium acetate, is also used; this reduces the pH to, say, 8 to 9 as opposed to 10 or more and enhances oxidation. Consequently the use of such a salt can reduce the mount of oxidising agent necessary in the subsequent step. Clearly the use of all liquid raw materials simplifies production. As indicated above, a maximum of 15 molar equivalents of amine species should be used. It has been found that, in general, the best results are obliged by using smaller concentrations of ammonia, typically from no more than 10 molar equivalents and, more particularly, no more than 8 molar equivalents. The resulting amine complex will be produced in aqueous solution generally having a pH from 8 to 10 and preferably from 9 to 10.

The amine complex is then oxidised. This is typically performed using hydrogen peroxide although aerial oxidation is also a possibility. 0.5 moles of hydrogen peroxide are required for stoichiometric purposes but, in practice, an excess of hydrogen peroxide is desirable. It has been found, though, that a large excess of hydrogen peroxide such as 2 moles is generally undesirable. This is because of the potential problem that the counter chloride ions present when cobaltous chloride is used as the starting material may be oxidised to chlorine causing a safety hazard. Thus the amount employed is typically from 0.5 to 1 moles.

According to one embodiment of the invention, conversion step (iii) is carried out with the corresponding carboxylic acid an hydride of formula $(R^1CO)_2O$.

Before this step is carried out, it has been found desirable to raise the pH of the solution resulting from step (ii), typically at a temperature from 50° C. to 80° C., especially 60° to 65° C., by the addition of an alkali such as sodium hydroxide or, for example, potassium hydroxide. Ammonium hydroxide is generally less desirable to use. This pH is suitably raised from 7 to 8.5 to, say, 9 to 12, preferably 10 to 11.5. It is believed that when the starting material is cobaltous chloride, this addition causes PACC to be converted to PAQC which can more readily be carboxylated. Thus in this preferred embodiment, in step (i) the increased pH due to ammonia addition is neutralised to enhance oxidation by a mildly acidic material while before carboxylation the pH is increased.

This solution is then desirably cooled, for example to room temperature (20°–25° C.) and then the carboxylic acid anhydride is added. Typically acetic anhydride is used for this purpose although peracetic acid and acetic acid can also be used. It should be added slowly since the reaction is significantly exothermic and it is desirable to cool the reaction vessel, for example to keep the temperature from exceeding, say, 40° C.

A particular feature of the process for the present invention is that the product of step (iii) can be obtained with very little impurities. In particular where cobaltous chloride is used as the starting material, little or no PACC is present. This product generally does not precipitate because of its very high solubility and can be isolated by evaporation.

According to a preferred embodiment of the invention, step (iii) is performed by increasing the amount of ammonium carboxylate added to the initial reaction mixture. Particularly good results are obtained by this method when the cobalt (II) salt is $Co(R^1COO)_2$, especially Where $R^1$ is methyl, or where the molar ratio of the ammonium carboxylate to the cobalt salt is from 3:1 to 4:1 and/or where the molar ratio of ammonia to the cobalt salt is from 4:1 to 7:1, particularly from 5:1 to 6:1.

An advantage of the preferred embodiment of the invention is it does not involve the use of strong bases which have to be used with care because of the danger of decomposition.

A further advantage is that the concentration of ammonia used is even less, reducing waste because there is less ammonia to distil off at the end of step (ii) and reducing the amount of washing required to remove the hexa ammonia complex (HAC) because less of this complex is formed.

According to another feature of the present invention, the X anion can be replaced by a different anion by a metathetical reaction in order that a new salt which is less soluble is obtained which may precipitate. In other words by replacing the chloride ion by a different "counter ion" which gives rise to a much less soluble complex it is possible to isolate the complex much more simply, for example by precipitation. Preferably the conversion of the counter ion is carried out before the reaction solution is allowed to cool. This is advantageous because larger crystal sizes are produced in the precipitate which are easier to filter. Numerous "counter ions" can be used for this purpose, of which the most preferred are the nitrate, fluoroborate and methane sulphonate (PAAN, PAAFB and PAAMS for the acetato complex) along with the perchlorate. Other anions which may be used include the sulphate, carbonate and various phosphates along with a variety of organic anions including the acetate, glutamate, succinate, malonate, fumarate and toluene sulphonate. Typical organic anions include those of the formula $R^2COO$ where $R^2$ represents an optionally hydroxy substituted alkyl or alkenyl group 1 to 18, for example 1 to 6, carbon atoms. The presence of a longer hydrocarbon chain will add to the hydrophobicity of the complex which will be useful in certain applications. It will be appreciated that the aim is to obtain a good yield of the salt in a readily collectable form. The reaction conditions should be adjusted accordingly. The fluoroborate and methane sulphonate of the pentammonium acetate complex are believed to be novel and form another aspect of the present invention.

When nitrate is to be used as the new counter ion, nitric acid or a suitable nitrate salt (e.g. an alkali metal nitrate) may be used in the conversion reaction. Preferably the molar ratio of nitric acid or nitrate salt to cobalt(II) starting material is from 2:1 to 5:1, more preferably 2:1 to 3:1.

It will be appreciated that the use of less ammonia or amine than has been suggested in the past is beneficial both in terms of processing and in terms of effluent management. Thus effluent which contains less amino compounds presents less of an environmental hazard than effluent containing higher concentrations. Similar comments apply to the use of relatively small concentrations of hydrogen peroxide. This lower concentration aids safety since the addition of large quantities of hydrogen peroxide tends to cause an effervescence which give rise to high oxygen contents in the flue.

Although the present discussion principally concerns the acetato cobalt complexes it will be appreciated that similar comments apply to other carboxylato complexes obtained by using higher anhydrides such as propionic anhydride in place of acetic anhydride.

The following Examples further illustrate the present invention.

EXAMPLE 1

Preparation of PAAC from cobalt (II) chloride

The following material were used:

| | |
|---|---|
| 32% ammonia solution | 98–135 g (see Table) |
| ammonium acetate | 92 g |
| 27% $CoCl_2$ solution | 190 g |
| 35% $H_2O_2$ solution | 29 g |
| 47% NaOH solution | 97–100 g (see Table) |
| $Ac_2O$ | 143 g |
| Total | 649–689 g |

The ammonia solution and ammonium acetate were charged to a stirred flask equipped with a condenser; the temperature of the resulting solution was 12°–15° C. The cobalt chloride solution was added over 10–15 minutes resulting in an exothermal reaction which raised the temperature of the solution to 35°–46° C. (see Table). The peroxide solution was then added over 10–15 minutes resulking in an exotherm to approximately 60° C. The solution was heated to 65° C. and the sodium hydroxide was added over 15–20 minutes exotherming 1°–2° C. After stirring 30–45 minutes with a controller set at 65° C. PACC was no longer detected and the solution was cooled to approximately 25° C. and the acetic anhydride was added over 45–60 minutes with cooling applied to keep the temperature below 40° C. The details are given in Table 1.

TABLE 1

| Ammonia solution/g | Cobalt exo-therm/ °C. | pH before $H_2O_2$ | pH before NaOH | NaOH solution/g | pH before $Ac_2O$ (25° C.) | Final pH | % Conversion | % Wt PAAC |
|---|---|---|---|---|---|---|---|---|
| 98 | 35 | 8.5 | 7.5 | 99 | 10.9 | 4.6 | 80 | 13.2 |
| 107 | 34 | 8.7 | 8.0 | 98 | 10.9 | 4.7 | 85 | 13.8 |

TABLE 1-continued

| Ammonia solution/g | Cobalt exo-therm/ °C. | pH before H$_2$O$_2$ | pH before NaOH | NaOH solution/g | pH before Ac$_2$O (25° C.) | Final pH | % Conversion | % Wt PAAC |
|---|---|---|---|---|---|---|---|---|
| 115 | 43 | 8.65 | 8.0 | 100 | 10.9 | 4.75 | 83 | 13.7 |
| 135 | 46 | 8.9 | 8.4 | 97 | 11.0 | 5.1 | 75 | 11.9 |

A bulk mixture was made from the solutions obtained. It analyzed as 13.7% Wt PAAC. It was used for precipitation trials. Three molar equivalents to Co of the acids shown in Table 2 were added to the solution with stirring; in each case an exotherm was observed. For nitrate and fluoroborate the slurry was gradually cooled to 5° C., filtered, washed with methanol and dried in a fan oven at 80° C. For methanesulphonate approximately 1.5 further mole equivalents of acid were added before precipitation started and the slurry treated as before. The overall yield assumes 85% conversion in solution.

TABLE 2

| Solution | Acid change | Dry Yield | Assay as PAAX | % of soln PAA isolated | Overall yield from CoCl$_2$ |
|---|---|---|---|---|---|
| 498 g | 81 g 70% HNO$_3$ | 82.0 g | 98.8% PAAN | 99.6 | 85% |
| 498 g | 197 g 40% HBF$_4$ | 79.5 g | 97.1% PAAFB | 82.3 | 70% |
| 353 g | 130 g 70% MeSO$_3$H | 62.4 g | 93.5% PAAMS | 84.0 | 71% |

The nitrate and fluoroborate additions resulted in immediate precipitation i.e. with the first few drops. The nitrate and methanesulphonate products filtered readily in a few minutes whereas the fluoroborate was more difficult to isolate by vac-filtration, taking over an hour. In separate tests we found that the methanesulphonate product precipitated if less methanesulphonic acid was added so long as an addition of strong acid was made e.g. HCl We also found that the use of sodium fluoroborate solution as precipitant leads to a big improvement in the ease of isolation of the fluoroborate. We confirmed that the nitrate and fluoroborate could be washed with water; the methanesulphonate cannot be because it has a solubility of approximately 25% compared to <1% for PAAN and PAAFB at room temperature.

EXAMPLE 2

PAAN Direct Process

The following materials were used:

| | |
|---|---|
| 32% ammonia solution | 345 g |
| ammonium acetate | 300 g |
| 27% CoCl$_2$ solution | 619 g |
| 35% H$_2$O$_2$ solution | 95 g |
| 47% NaOH solution | 320 g |
| Ac$_2$O | 464 g |
| (Sub-total 1) | (2143 g) |
| 70% HNO$_3$ solution | 234 g |
| Reactor total | 2377 g |

The ammonia solution at 25° C. and ammonium acetate were charged to a stirred 3 l RB Quickfit flask equipped with a condenser and reaction temperature-controller; after stirring 5 minutes the resulting solution registered 5° C. The cobalt chloride solution was added over 15 minutes in a steady stream resulting in an exotherm to 41° C. after approximately ¾ of the addition; at the end of the addition the temperature in the flask was 38° C. After stirring 40 minutes the red solution was at 33° C. and registered pH 8.66; a trace of solid was observed in the flask. The hydrogen peroxide solution was added over 50 minutes during which time the temperature in the flask rose to 56° C. Early in the addition each drop produced a vigorous effervescence upon contact with the flask contents; towards the end the effervescence at the point of contact diminished significantly being replaced by a gentle effervescence across the surface and the solution developed a more intense red colour. The mantle was set to heat to 65° C.; at 60° C. the solution registered pH 7.9 and the caustic soda addition was started; it lasted 15 minutes during which time an exotherm was observed and the temperature peaked at 70° C. After stirring a further 30 minutes the temperature had dropped back to 65° C. and the solution registered pH 10.6 having peaked at 11.1; no solid was observed in the flask. After cooling to 27° C. the solution registered pH 11.2. The acetic anhydride was added over 110 minutes whilst the flask was immersed in a water bath (changed a few times); the maximum temperature observed was 38° C. After the addition there was no evidence of continuing exotherm and the pH was stable at 4.7. The solution was a deep red colour and no solid was observed in the flask. The flask was weighed and found to contain 2134 g nett, mass balance −9 g. A small sample was taken and analyzed by HPLC, <0.1% Wt. "PAC" was detected and the solution assayed as 14.8% "PAAC" (Conversion=88% on Co). The nitric acid solution was added at a steady rate over 35 minutes; an exotherm was observed as the flask contents rose to 45° C. with no cooling applied during the addition a red solid precipitated. The slurry was cooled to 23° C. over 60 minutes; it registered pH 3.5. It filtered with ease through a No1 porosity sintered-glass Buchner funnel under vacuum. The cake was washed with 2×approximately 200 mls ice cold water and left in the funnel for approximately 30 minutes.

Yield=2313 g combined liquor; 407 g wet-cake

The wet-cake was dried in a fan over at 80° C. for 2 hours, and ground in a mortar and pestle before analysis;

| | | | |
|---|---|---|---|
| Yield = | 351 g | Assay = | 100.2% as PAAN < 0.2% PAC i.e. 1.08 moles; 83% Yield on Cobalt. |

The liquor registered pH 3.6. It was analyzed by HPLC and found to contain product equivalent to 20 g PAAN, i.e. 5% of Co charge. The nitric acid charge equates to 2 mole equivalents to Co. i.e. ⅔ the amount used in Example 1. In similar experiments from cobalt acetate we observed quantitative precipitation if the solutions were acidified to pH1; the pH drops rapidly below pH 3 so a small increase in nitric acid addition would probably maximise the yield. The liquor has a brown-black colour; it darkens during the nitric acid addition. It has a strong odor of acetic acid and the following approximate composition calculated by difference from the charges and dried product, assuming for the time being that "non-PAA cobalt" is present as HAC complex;

Combined liquor+washings

| PAAN | 0.06 moles | 20 g | 0.87% |
|---|---|---|---|
| HAC | 0.16 moles | 59 g | 2.5% |
| sodium chloride | 1.94 moles | 113 g | 4.9% |
| sodium nitrate | 0.44 moles | 37 g | 1.6% |
| sodium acetate | 1.42 moles | 116 g | 5.0% |
| ammonium acetate | 3.68 moles | 283 g | 12% |
| acetic acid | 6.8 moles | 408 g | 18% |
| Total solids | | 1036 g | 44.8% |

The complexes contain 10 g cobalt i.e. 0.43% Wt. in the liquor.

EXAMPLE 3

PAAMS Direct Process

The following materials were used:

| 32% ammonia solution | 398 g |
|---|---|
| ammonium acetate | 347 g |
| 27% CoCl$_2$ solution | 714 g |
| 35% H$_2$O$_2$ solution | 109 g |
| 47% NaOH solution | 370 g |
| Ac$_2$O | 536 g |
| (Sub-total 1) | (2474 g) |
| 36% HCl solution | 350 g |
| 70% MeSO$_3$H solution | 411 g |
| Reactor total | 3235 g |

There were no significant differences to Example 2 up to the end of the anhydride addition when the flask contained 2461 g solution with pH 4.8 and an assay of 14.9% PAAC i.e. 89% conversion from Cobalt.

With the flask contents at 26° C. the hydrochloric acid addition was made over 20 minutes whilst cooling in a water bath to 24° C. when the solution registered pH 3.5. The methanesulphonic acid solution was added over 45 minutes accompanied by a raise in temperature in the flask to 29° C. and a drop in pH to <1. After approximately 80% of the addition the product "dropped out" of solution and an exotherm was observed to 34° C. After cooling to 15° C. the slurry was filtered through two No1 porosity sintered-glass Buchner funnels under vacuum, the cake was washed with a total of 600 mls methanol and left in the funnel overnight then dried for an hour in a fan oven at 80° C., and ground in a mortar and pestle before analysis.

Yield=2313 g combined liquor; 440 g Dry product
Assay=97.1% as PAAMS, approximately 3% "PAC"
i.e. 1.09 moles; 84% Yield on Cobalt.

EXAMPLE 4

PAAFB Direct Process

A batch of solution was prepared as for PAAMS (Example 3) with c. 3.5 hours for the anhydride addition. The yield was 2481 g with pH 4.83 and assay 14.6% PAAC, i.e. 88% conversion.

The desired product was made by sodium fluoroborate precipitation and water washing from a composite sample of "PAA" solutions prepared in the presence of chloride and acetate ions, i.e. samples from both cobalt salts+"opposite" buffering add. The "PAA" solution assayed 13.0% as PAAC and contained practically no PACC. The percentage yield for this step was 70%, i.e. percentage of solution "PAA" found in the washed and dried PAAFB; 239 g Dry product; Assay=101% as PAAFB, <0.2% "PAC".

EXAMPLE 5

A series of experiments were performed on cobalt (II) acetate tetrahydrate with ammonium chloride at the same pH's and temperatures as in Example 1. The conversions were not as good even if water was added to the same overall strength, namely 66% conversion using 'all-crystals' and 75% with added water (either as cobalt acetate solution, or diluted ammonia reactants+cobalt acetate crystals). The pH's after acetic anhydride addition were approximately 4.5 as expected.

Further experiments were performed at 8 moles total ammonia species per mole cobalt with other acid buffers to give solutions of Co (II) complexes with pH approximately 8.7 prior to oxidation:

| Cobalt (II) salt | Acid | Moles ammonia | Moles amm. salt |
|---|---|---|---|
| Chloride | HCl | 5.7 | 2.3 |
| Chloride | AcOH | 5.0 | 3.0 |
| Acetate | HCl | 5.4 | 2.6 |
| Acetate | AcOH | 4.0 | 4.0 |
| Acetate | H$_2$SO$_4$ | 5.2 | 1.4 |
| Acetate | MeSO$_3$H | 5.85 | 2.15 |
| Acetate | HNO$_3$ | 4.5 | 3.5 |

Following the same method as before with all acetate species the following results were obtained;

| Moles Ac$_2$O:Co | pH | % Conversion |
|---|---|---|
| 3 | 5.6 | 61 |
| 3/5 | 5.6 | 75 |
| 5 | 5 | 78 |

Experiments with 3 moles anhydride and sulphate or methanesulphonate buffering prepared in-situ resulted in conversions of 61 and 59% respectively in solutions of pH 4.7 and 4.65. Experiments with ammonium nitrate, added as solid, resulted in precipitation of product as 'PAA' formed; the final mixtures were acidified to pH 1 when PAAN was collected quantitatively, i.e. no 'PAA' remained in the liquors. The best yield was 69% from 3 moles anhydride; the slurry prior to nitric acid addition registered pH 4.8.

EXAMPLE 6

Preparation of PAAN from Cobalt (II) Acetate

The following material was used:

| Ammonium acetate | 162 g |
|---|---|
| 28% Ammonia Solution | 233 g |
| Cobalt (II) acetate.4H$_2$O | 87 g |
| 35% H$_2$O$_2$ | 34 g |
| (Solution sub-total) | (516 g) |

| | |
|---|---|
| 45% NaNO₃ | 265 g |
| Total | 781 g |

Cobalt acetate was quickly added to freshly prepared ammonia buffer at 11° C. to form a clear solution at a temperature of 26° C. The hydrogen peroxide solution was then added over 20 minutes without cooling during which time the temperature of the solution rose from 26° C. to 49° C. The solution was then stirred for one hour. After stirring, the temperature of the solution was 33° C. It was then heated to a temperature of 80° C. It was then maintained at this temperature for six hours. After cooling to 21° C., the sodium nitrate solution was added over a period of 20 minutes. 20 minutes after the addition of the sodium nitrate solution, the solution was cooled and after an hour, it was filtered and washed with iced water. The product filtered slowly and gave a very wet cake (approximately 30% water) which was dried in an oven at 70° C.

Results and Analysis

The mass balance showed that 83 g was lost per mole of cobalt. The conversion of cobalt based on the mount of PAAA obtained was 90.5%. In the assay of the dry product was found 96.7% by weight of PAAN and 3.9% by weight of HAN ($[Co^{III}(NH_3)_6](NO_3)_3$). The dry yield of PAAN with respect to the mount of cobalt used was 86%. The recovery of PAA from solution was 95%.

EXAMPLE 7

Preparation of PAAA from Cobalt (II) Acetate using Aerial Oxidation

The following material was used:

| | |
|---|---|
| Ammonium acetate | 578 g |
| 28% Ammonia solution | 835 g |
| Cobalt (II) acetate.4H₂O | 311 g |
| Solution total | 1724 g |

Cobalt acetate was added quickly to freshly prepared ammonia buffer without cooling. The resultant solution was clear and had a temperature of 23° C. Air was then bubbled through the solution at a rate of 800 ml/min and was left on overnight. After approximately 20 hours, the air supply was stopped and the solution was heated to 80° C. and this temperature was maintained for six hours. At the end of the heating, the solution was cooled.

Results and Analysis

The mass balance showed that 94 g was lost per mole of cobalt in the experiment. The conversion rate of cobalt based on the PAAA assay was 85.8%.

EXAMPLE 8

Preparation of PAAA from Cobalt (II) Acetate

The following material was used:

| | |
|---|---|
| Ammonium acetate | 216 g |
| 32% Ammonia solution | 234 g |
| Cobalt (II) acetate.4H₂O | 199 g |
| 35% hydrogen peroxide | 58 g |
| Solution total | 707 g |

Cobalt acetate was added to freshly prepared ammonia buffer quickly without cooling. The resultant solution was clear and had a temperature of 28° C. Peroxide solution was then added over a period of 50 minutes without cooling. The resultant solution which had a temperature of 59° C. was then stirred for 40 minutes. The stirred solution was heated to 80° C. and this temperature was maintained for six hours. The solution was then cooled.

Results and Analysis

The mass balance showed that 5 g was lost per mole of cobalt in the experiment. The conversion rate of cobalt based on the PAAA assay was 88.9%.

EXAMPLE 9

Preparation of PAAA from Cobalt (II) Acetate

The following material was used:

| | |
|---|---|
| Ammonium acetate | 1011 g |
| 32% Ammonia solution | 1095 g |
| Cobalt (II) acetate.4H₂O | 934 g |
| 35% hydrogen peroxide | 219 g |
| Solution total | 3259 g |

Cobalt acetate was added to freshly prepared ammonia buffer quickly without cooling. The resultant solution had a temperature of 26° C. and after 60 minutes, the hydrogen peroxide solution was added over a period of 3¾ hours. Frothing was observed towards the end of the peroxide addition and water was used to wash down the condenser. After the addition of peroxide, the solution was maintained at a temperature of 46° C. for 20 minutes. It was then heated to 80° C. and maintained over night before being cooled.

Results and Analysis

The conversion rate of cobalt based on the PAAA assay was 86.4%.

EXAMPLE 10

Preparation of PAAA from Cobalt (II) Acetate using Aerial Oxidation

The following material was used:

| | |
|---|---|
| Ammonium acetate | 606 g |
| 28% Ammonia Solution | 657 g |
| Cobalt (II) acetate.4H₂O | 560 g |
| Solution total | 1823 g |

Cobalt acetate was added to freshly prepared ammonia buffer quickly without cooling. The resultant solution was clear and had a temperature of 27° C. After 55 minutes, air was bubbled through the solution at a rate of 1800 ml/min and the air was left on overnight. Approximately 20 hours later, the air supply was stopped and the solution was heated to 80° C. and maintained at this temperature for 6 hours before being cooled.

Results and Analysis

The mass balance showed that 32 g was lost per mole of cobalt in the experiment. The conversion rate of cobalt based on the PAAA assay was 70.0%.

EXAMPLE 11

Precipitation with sodium nitrate of the product of Example 9

The following material was used:

| Example 9 solution | 436 g |
|---|---|
| 45% sodium nitrate | 189 g (First aliquot) |
| 45% sodium nitrate | 66 g (Second aliquot) |
| Slurry total | 691 g |

The first aliquot of sodium nitrate was added over a period of 55 minutes without cooling. Precipitation started with the first few drops and was mildly exothermic. The final temperature of the solution was 30° C. and an assay of the supernatant after addition of the first aliquot showed that less than 5% of PAA remained in the solution. The second aliquot of sodium nitrate was then added after a wait of 35 minutes over a period of 15 minutes. An assay of the supernatant after the addition of the second aliquot showed that an insignificant mount of PAA remained in the solution. After one hour, the precipitate was filtered and washed with 200 ml of ice water.

Results and Analysis

In the assay of the dry product was found 92.7% by weight of PAAN and 6.5% by weight of HAN. The dry yield of PAAN with respect to the amount of cobalt used was 82%. The recovery of PAA from solution was 95%.

EXAMPLE 12

Precipitation with nitric acid of the product of Example 9

The following material was used:

| Example 9 solution | 523 g |
|---|---|
| 68% nitric acid | 111 g |
| 68% nitric acid | 39 g |
| Slurry total | 673 g |

The first aliquot of nitric acid was added over a period of 20 minutes without cooling. Precipitation started with the first few drops and was highly exothermic. The final temperature was 59° C. An assay of the supernatant after the addition of the first aliquot showed that less than 5% of PAA remained in the solution. Cooling was then applied for ½ hour until a temperature of 18° C. was reached and then the second aliquot was added over a period of 10 minutes. An assay of the supernatant after the addition of the second aliquot showed that an insignificant trace of PAA remained in the solution. The product was cooled for 40 minutes then filtered and washed with 240 ml iced water.

Results and Analysis

In the assay of the dry product was found 94.6% by weight of PAAN and 6.8% by weight of HAN. The dry yield of PAAN with respect to the amount of cobalt used was 86%. The recovery of PAA from solution was 99.5%.

We claim:

1. A process for preparing a cobalt III complex which comprises:

(i) treating a divalent cobalt salt of formula $Co^{II}X_{2/n}$ where n is the valency of an anion X, with up to 15 molar equivalents of ammonia or an amine;

(ii) oxidising the resulting amine complex;

(iii) converting the oxidised complex to the corresponding carboxylate of formula $[Co^{III}(NR_3)_5R^1COO]X_{2/n}$ where each R, which may be the same or different, represents hydrogen or an optionally substituted hydrocarbon group and $R^1$ represents an alkyl or alkenyl group of 1 to 18 carbon atoms, at a pH above 8.5; and optionally (iv) replacing the X ion by a different anion by a metathetical reaction.

2. A process according to claim 1 in which the divalent cobalt salt is cobaltous acetate.

3. A process according to claim 1 or 2 in which ammonia is used in step (i).

4. A process according to claim 3 in which the ammonia is added as ammonium acetate.

5. A process according to claim 4 in which the molar ratio of ammonia to cobalt salt is from 5:1 to 6:1.

6. A process according to claim 4 in which the molar ratio of ammonium salt to the cobalt salt is from 3:1 to 4:1.

7. A process according to claim 1 in which step (ii) is carried out with hydrogen peroxide.

8. A process according to claim 7 in which the hydrogen peroxide is used in an amount from 0.5 to 1 moles per mole of complex.

9. A process according to claim 1 in which after step (ii) and before (iii) the pH is raised to 9 to 12 by the addition of alkali metal hydroxide and/or ammonium hydroxide.

10. A process according to claim 1 in which step (iii) is carried out using the corresponding carboxylic acid anhydride of formula $(R^1CO)_2O$.

11. A process according to claim 1 in which R represents methyl.

12. A process according to claim 1 in which step (iv) is carried out wherein the new ion X is the nitrate, fluoroborate, methane sulphonate or perchlorate.

13. A cobalt complex of the formula $[Co^{III}(NR_3)_5R^1COO]X_{2/n}$ where each R, which may be the same or different, represents hydrogen or an unsubstituted or substituted hydrocarbon group, $R^1$ represents methyl, X represents fluoroborate or methane sulphonate and n is the valency of X.

14. A process according to claim 3 in which the molar ratio of ammonia to cobalt salt is from 5:1 to 6:1.

15. A process according to claim 3 in which the molar ratio of ammonium salt to the cobalt salt is from 3:1 to 4:1.

* * * * *